United States Patent
Heims et al.

(10) Patent No.: US 10,799,216 B1
(45) Date of Patent: *Oct. 13, 2020

(54) WAVE GUIDE WITH ELECTRIC POWER CONDUIT

(71) Applicant: Raytheon Technologies Corporation, Farmington, CT (US)

(72) Inventors: Eric J. Heims, Avon, CT (US); Ryan K. Snyder, Glastonbury, CT (US); Kurt J. Sobanski, Glastonbury, CT (US)

(73) Assignee: Raytheon Technologies Corporation, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/408,538

(22) Filed: May 10, 2019

Related U.S. Application Data

(63) Continuation of application No. 15/480,757, filed on Apr. 6, 2017, now Pat. No. 10,307,138.

(51) Int. Cl.
| | | |
|---|---|---|
| *A61B 8/00* | (2006.01) | |
| *A61B 8/08* | (2006.01) | |
| *A61B 8/13* | (2006.01) | |
| *A61B 8/14* | (2006.01) | |

(Continued)

(52) U.S. Cl.
CPC ............. *A61B 8/485* (2013.01); *A61B 8/13* (2013.01); *A61B 8/14* (2013.01); *A61B 8/4483* (2013.01); *A61B 8/5207* (2013.01); *F01D 21/003* (2013.01); *H01P 1/042* (2013.01); *F05D 2260/80* (2013.01); *F23N 2223/38* (2020.01);

(Continued)

(58) Field of Classification Search
CPC .. A61B 8/485; A61B 8/13; A61B 8/14; A61B 8/4483; A61B 8/5207; F01D 21/003; H01P 1/042; F23N 2223/38; F23N 2900/05004; F23N 2900/05005; F05D 2260/80
USPC ........................................................ 333/137
See application file for complete search history.

(56) References Cited

U.S. PATENT DOCUMENTS

| 8,295,665 | B2 | 10/2012 | Herbst | |
|---|---|---|---|---|
| 8,319,104 | B2 * | 11/2012 | Camp, II | ............... H01B 11/04 |
| | | | | 174/113 C |
| 9,136,045 | B2 * | 9/2015 | Burke | ................... H01B 11/22 |

(Continued)

FOREIGN PATENT DOCUMENTS

| EP | 2189628 | 5/2010 |
|---|---|---|
| EP | 2961087 | 12/2015 |

(Continued)

OTHER PUBLICATIONS

European Search Report for Application No. 18166039.0 dated Oct. 17, 2018.

*Primary Examiner* — Robert J Pascal
*Assistant Examiner* — Kimberly E Glenn
(74) *Attorney, Agent, or Firm* — Carlson, Gaskey & Olds, P.C.

(57) ABSTRACT

A wave guide assembly for a control and diagnostic system for a machine includes a housing defining an exterior surface and an internal cavity extending between distal ends. At least one wave guide within the internal cavity defines a wave propagation passage for at least one wave form signal. At least one conductor within the internal cavity is separate from the wave guide. A control and diagnostic system for a machine and a gas turbine engine are also disclosed.

18 Claims, 10 Drawing Sheets

(51) Int. Cl.
*H01P 1/04* (2006.01)
*F01D 21/00* (2006.01)

(52) U.S. Cl.
CPC ............... *F23N 2900/05004* (2013.01); *F23N 2900/05005* (2013.01)

(56) References Cited

U.S. PATENT DOCUMENTS

2007/0102279 A1    5/2007  Novak
2008/0246470 A1*  10/2008  Kahlman ............... B82Y 25/00
                                                    324/234

FOREIGN PATENT DOCUMENTS

| | | |
|---|---|---|
| EP | 3291363 | 3/2018 |
| GB | 2065410 | 6/1981 |
| WO | 2015130563 | 9/2015 |

* cited by examiner

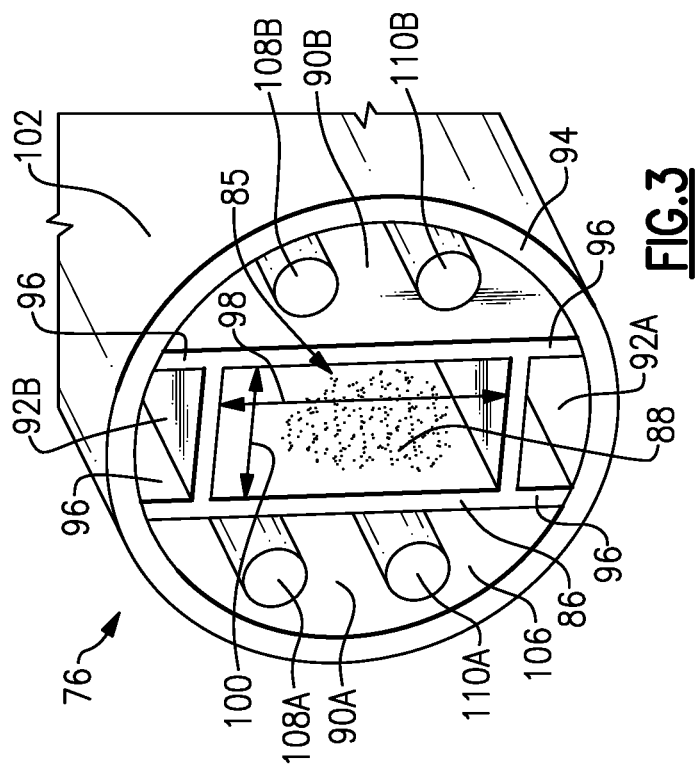
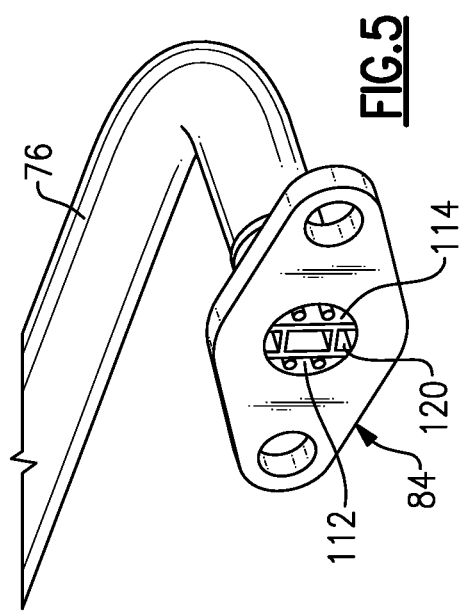
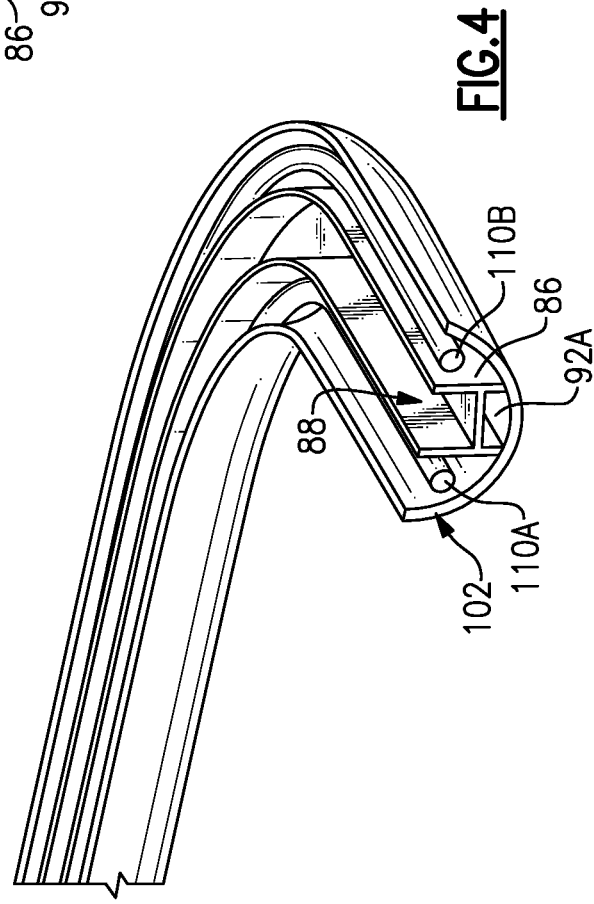
FIG.3
FIG.5
FIG.4

WAVE GUIDE WITH ELECTRIC POWER CONDUIT

CROSS-REFERENCE TO RELATED APPLICATIONS

This application is a continuation of U.S. patent application Ser. No. 15/480,757, filed Apr. 6, 2017.

BACKGROUND

A gas turbine engine typically includes a fan section, a compressor section, a combustor section and a turbine section. Air entering the compressor section is compressed and delivered into the combustion section where it is mixed with fuel and ignited to generate a high-speed exhaust gas flow. The high-speed exhaust gas flow expands through the turbine section to drive the compressor and the fan section. The compressor section typically includes low and high pressure compressors, and the turbine section includes low and high pressure turbines.

Devices that are used to control and sense operation of the gas turbine engine communicate with a controller through many different wires that are gathered in a wire harness. The wire harness includes each of the individual wires required to provide power and communication. In many instances, dual wires are routed to a device or sensor to provide a required redundancy in case of failure. Moreover, many of the wires require shielding to assure reliable transmission of communication signals. The number of wires along with the accompanying shielding, and braiding a mass a significant amount of weight. Irregular shapes from the bundling of wires creates challenges in supporting and securing the wire harness throughout engine.

Turbine engine manufacturers continue to seek further improvements to engine performance including improvements in reliability as well as in thermal, transfer and propulsive efficiencies.

SUMMARY

In a featured embodiment, a wave guide assembly for a control and diagnostic system for a machine includes a housing defining an exterior surface and an internal cavity extending between distal ends. At least one wave guide within the internal cavity defines a wave propagation passage for at least one wave form signal. At least one conductor within the internal cavity is separate from the wave guide.

In another embodiment according to the previous embodiment, includes an end fitting attached to each end of the housing.

In another embodiment according to any of the previous embodiments, includes a coupling branching the wave propagation passage into two separate paths extending in different direction. The coupling includes three ends with a wave propagation passage and one of an electrical power conductor and an optic fiber extending to each of the three ends.

In another embodiment according to any of the previous embodiments, each of the three ends of the coupling includes a face and each face includes a connector corresponding with the at least one conductor.

In another embodiment according to any of the previous embodiments, the wave propagation passage includes a rectangular wave propagation passage in cross-section within the internal cavity.

In another embodiment according to any of the previous embodiments, the wave propagation passage includes a circular wave propagation passage in a cross-section within the internal cavity.

In another embodiment according to any of the previous embodiments, the wave propagation passage is a separate part inserted into the housing.

In another embodiment according to any of the previous embodiments, includes a dielectric within the wave propagation passage.

In another embodiment according to any of the previous embodiments, the wave propagation passage defines a size corresponding with a desired frequency range of the wave form signal.

In another embodiment according to any of the previous embodiments, the housing includes a tube with a circular external cross-section and the wave propagation passage is contained within the cross-section.

In another embodiment according to any of the previous embodiments, outer walls of the wave propagation passage cooperate with interior walls of the internal cavity to define conductor passages for at least one of an electrical conductor and an optic fiber.

In another embodiment according to any of the previous embodiments, where the conductor passages are defined on either side of the wave guide.

In another embodiment according to any of the previous embodiments, the conductor includes one of an electrical conductor and an optic fiber disposed in each of the conductor passages.

In another embodiment according to any of the previous embodiments, includes support members supporting the wave propagation passage within the internal cavity. The support members define cavities separated from the conductor passages.

In another featured embodiment, a control and diagnostic system for a machine includes a main transceiver mounted proximate the machine. The transceiver generates and receives radio frequency waves corresponding to information for control and monitoring of engine operation. A housing defines an exterior surface and an internal cavity extends between distal ends. A wave guide is within the internal cavity defining a wave propagation passage for a wave form signal, and a conductor passage for at least one conductor extending within the internal cavity separate from the wave guide. At least one remote transceiver is attached to an end of the wave guide assembly and in communication with the main transceiver through a wave form signal communicated through the wave guide.

In another embodiment according to any of the previous embodiments, includes an end fitting attached to each end of the housing for coupling the housing to the main transceiver at one end and to the at least one remote transceiver at another end and a coupling branching the wave propagation passage into two separate paths extending in different directions to a corresponding one of the at least one transceivers. The coupling includes three ends.

In another featured embodiment, a gas turbine engine includes a control and diagnostic system which include a main transceiver mounted proximate the gas turbine engine. The main transceiver generates and receives radio frequency waves corresponding to information for control and monitoring of engine operation. A wave guide assembly includes a tubular housing defining an exterior surface and an internal cavity extending between distal ends. A wave guide within the internal cavity defines a transmission pathway for a wave form signal, and a passage for a conductor extending within the internal cavity separate from the wave guide. At least one remote transceiver is attached to an end of the wave guide assembly and in communication with the main transceiver through a wave form signal communicated through the wave guide.

In another embodiment according to the previous embodiment, includes an end fitting attached to each end of the housing for coupling the housing to the main transceiver. The at least one remote transceiver and to a coupling, the coupling includes three ends branching the wave propagation passage into two separate paths extending in different directions.

In another embodiment according to any of the previous embodiments, the wave guide is a separate part inserted into the tubular housing.

In another embodiment according to any of the previous embodiments, wave guide includes an internal cross-section that defines a size corresponding with a desired frequency range of a wave form signal.

Although the different examples have the specific components shown in the illustrations, embodiments of this disclosure are not limited to those particular combinations. It is possible to use some of the components or features from one of the examples in combination with features or components from another one of the examples.

These and other features disclosed herein can be best understood from the following specification and drawings, the following of which is a brief description.

BRIEF DESCRIPTION OF THE DRAWINGS

FIG. 3 is a cross-sectional view through a wave guide tube.

FIG. 4 is a sectional view of a portion of the wave guide tube.

FIG. 5 is a perspective view of an end fitting.

DETAILED DESCRIPTION

Figure 1:
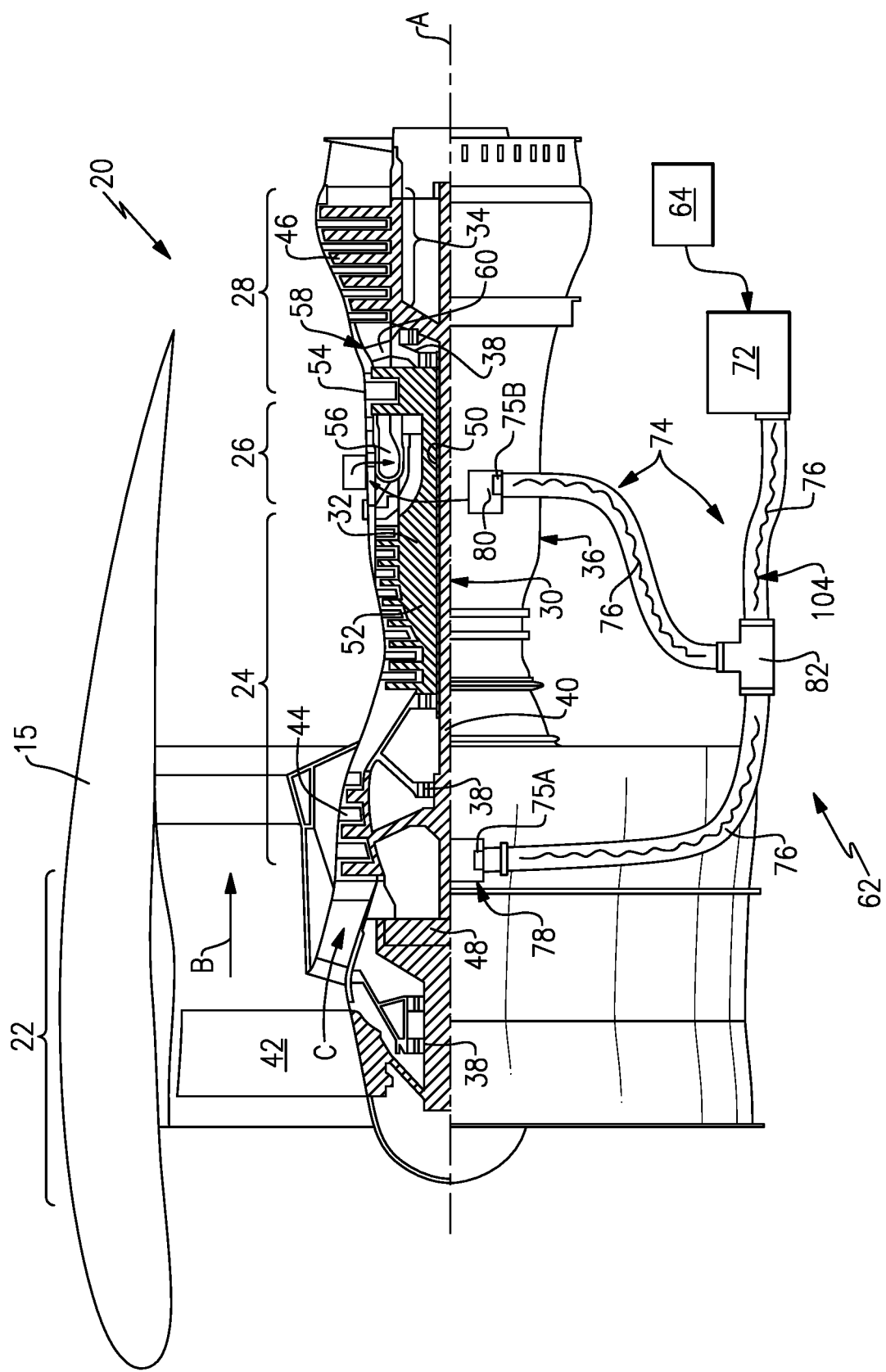
FIG. 1 is a schematic view of an example gas turbine engine including an example control and diagnostic system embodiment.

FIG. 1 schematically illustrates a gas turbine engine 20. The gas turbine engine 20 is disclosed herein as a two-spool turbofan that generally incorporates a fan section 22, a compressor section 24, a combustor section 26 and a turbine section 28. Alternative engines might include an augmentor section (not shown) among other systems or features. The fan section 22 drives air along a bypass flow path B in a bypass duct defined within a nacelle 15, and also drives air along a core flow path C for compression and communication into the combustor section 26 then expansion through the turbine section 28. Although depicted as a two-spool turbofan gas turbine engine in the disclosed non-limiting embodiment, it should be understood that the concepts described herein are not limited to use with two-spool turbofans as the teachings may be applied to other types of turbine engines including three-spool architectures.

The exemplary engine 20 generally includes a low speed spool 30 and a high speed spool 32 mounted for rotation about an engine central longitudinal axis A relative to an engine static structure 36 via several bearing systems 38. It should be understood that various bearing systems 38 at various locations may alternatively or additionally be provided, and the location of bearing systems 38 may be varied as appropriate to the application.

The low speed spool 30 generally includes an inner shaft 40 that interconnects a fan 42, a first (or low) pressure compressor 44 and a first (or low) pressure turbine 46. The inner shaft 40 is connected to the fan 42 through a speed change mechanism, which in exemplary gas turbine engine 20 is illustrated as a geared architecture 48 to drive the fan 42 at a lower speed than the low speed spool 30. The high speed spool 32 includes an outer shaft 50 that interconnects a second (or high) pressure compressor 52 and a second (or high) pressure turbine 54. A combustor 56 is arranged in exemplary gas turbine 20 between the high pressure compressor 52 and the high pressure turbine 54. A mid-turbine frame 58 of the engine static structure 36 is arranged generally between the high pressure turbine 54 and the low pressure turbine 46. The mid-turbine frame 58 further supports bearing systems 38 in the turbine section 28. The inner shaft 40 and the outer shaft 50 are concentric and rotate via bearing systems 38 about the engine central longitudinal axis A which is collinear with their longitudinal axes.

The core airflow is compressed by the low pressure compressor 44 then the high pressure compressor 52, mixed and burned with fuel in the combustor 56, then expanded over the high pressure turbine 54 and low pressure turbine 46. The mid-turbine frame 58 includes airfoils 60 which are in the core airflow path C. The turbines 46, 54 rotationally drive the respective low speed spool 30 and high speed spool 32 in response to the expansion. It will be appreciated that each of the positions of the fan section 22, compressor section 24, combustor section 26, turbine section 28, and fan drive gear system 48 may be varied. For example, gear system 48 may be located aft of combustor section 26 or even aft of turbine section 28, and fan section 22 may be positioned forward or aft of the location of gear system 48.

The engine 20 in one example is a high-bypass geared aircraft engine. In a further example, the engine 20 bypass ratio is greater than about six (6), with an example embodiment being greater than about ten (10), the geared architecture 48 is an epicyclic gear train, such as a planetary gear system or other gear system, with a gear reduction ratio of greater than about 2.3 and the low pressure turbine 46 has a pressure ratio that is greater than about five. In one disclosed embodiment, the engine 20 bypass ratio is greater than about ten (10:1), the fan diameter is significantly larger than that of the low pressure compressor 44, and the low pressure turbine 46 has a pressure ratio that is greater than about five 5:1. Low pressure turbine 46 pressure ratio is pressure measured prior to inlet of low pressure turbine 46 as related to the pressure at the outlet of the low pressure turbine 46 prior to an exhaust nozzle. The geared architecture 48 may be an epicycle gear train, such as a planetary gear system or other gear system, with a gear reduction ratio of greater than about 2.3:1. It should be understood, however, that the above parameters are only exemplary of one embodiment of a geared architecture engine and that the present invention is applicable to other gas turbine engines including direct drive turbofans.

A significant amount of thrust is provided by the bypass flow B due to the high bypass ratio. The fan section 22 of the engine 20 is designed for a particular flight condition— typically cruise at about 0.8 Mach and about 35,000 feet (10,668 meters). The flight condition of 0.8 Mach and 35,000 ft (10,668 meters), with the engine at its best fuel consumption—also known as "bucket cruise Thrust Specific Fuel Consumption ('TSFC')"—is the industry standard parameter of lbm of fuel being burned divided by lbf of thrust the engine produces at that minimum point. "Low fan pressure ratio" is the pressure ratio across the fan blade alone, without a Fan Exit Guide Vane ("FEGV") system. The low fan pressure ratio as disclosed herein according to one non-limiting embodiment is less than about 1.45. "Low corrected fan tip speed" is the actual fan tip speed in ft/sec divided by an industry standard temperature correction of $[(\text{Tram } °\text{ R})/(518.7° \text{ R})]^{0.5}$. The "Low corrected fan tip speed" as disclosed herein according to one non-limiting embodiment is less than about 1150 ft/second (350.5 meters/second).

The disclosed gas turbine engine includes a control and diagnostic system 62 that communicates information between various sensors, actuators and components of the gas turbine engine 20. It should be understood, that although a gas turbine engine 20 is disclosed and explained by way of example that other machines that require control and diagnostics such as internal combustion engines utilized in automobiles and aircraft are also within the contemplation of this disclosure. Moreover, other machines that operate and that are subject to harsh environments would also benefit from this disclosure and are within the contemplation of this disclosure.

The example control and diagnostic system 62 includes a main transceiver 72 coupled to a wave guide assembly 74. The example main transceiver 72 generates and receives wave form signals. In this disclosure wave form signals includes microwave high frequency signals, radio frequency signals and any other wave form format that can be utilized to send and receive information and commands through the wave guide assembly 74 to components and sensors throughout the gas turbine engine 20.

In the disclosed example embodiment, the wave guide assembly 74 defines a transmission pathway for wave form signal communication with sensor 78 and component 80. As appreciated, the sensor 78 and the component 80 are representative of various components and devices utilized through the engine to sense current engine operating conditions and control operation of the engine. The engine 20 will include many sensors 78 and many components 80 arranged throughout the engine that generate or receive information and commands from an engine controller 64. The engine controller 64 can be part of full authority digital engine control, commonly known as a FADEC, or receive information from the FADEC. The main transceiver 72 may be contained within or external to the engine controller 64. Each of the sensors 78 and the component 80 includes a second or remote transceiver 75a, 75b that communicates with the main transceiver 72 through wave form signals routed through the wave guide assembly 74. The engine controller 64 may also contain within itself or an external unit, diagnostic functions capable of assessing the system health and system degradation.

The wave guide assembly 74 defines a communication path through which wave signals schematically shown at 104 are routed between the main transceiver 72 and various remote transceivers 75a, 75b associated with each sensor 78 and component 80. It should be appreciated, that the engine 20 may include several separate wave guide assemblies 74 providing communication pathways for different systems. Moreover, each wave guide assembly 74 may provide communication from different main transceivers 72.

The disclosed example wave guide assembly 74 includes wave guide tubes 76 coupled to the main transceiver 72 on one end and the sensor 78 or component 80 on other ends. The example wave guide assembly 74 defines the passages that are utilized to communicate with the various devices within the gas turbine engine 20. Rather than including individual electric conductor or wires separately run between each of the components, the example wave guide assembly 74 provides a common wave guide passageway for each of the components 80 or sensors 78. The main transceiver 72 transmits and receives multiple wave form frequencies through the same passageway for communicating with different sensors and components concurrently.

The wave guide tube 76 includes multiple tubes 76 of various shapes and lengths to extend to sensors and actuators throughout the engine 20. The wave guide tubes 76 are secured together at a coupling 82 such that a single passage is split into different passages that extend in different directions.

Figure 2:
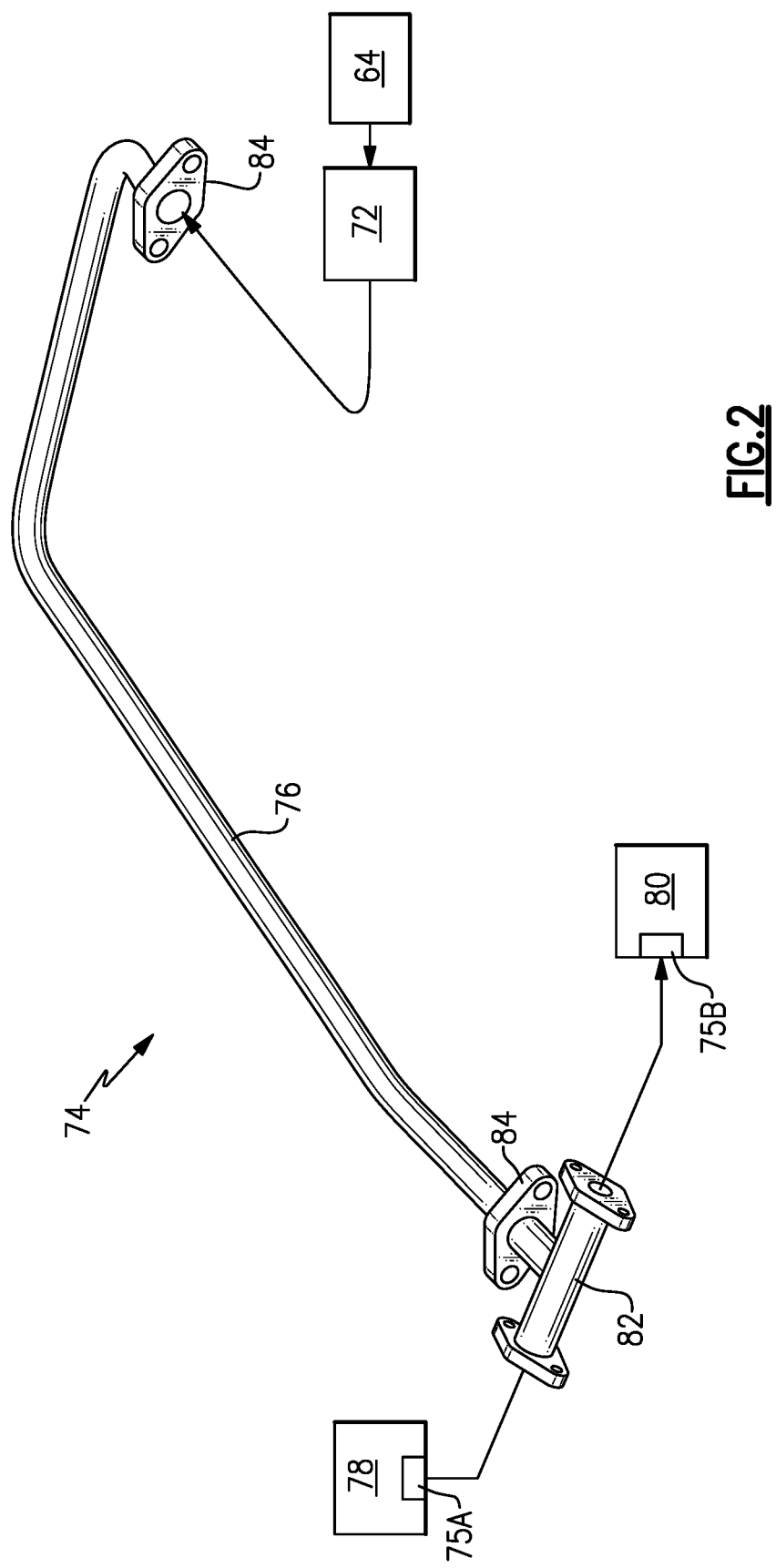
FIG. 2 is a perspective view of an example wave guide assembly.

Referring to FIG. 2 with continued reference to FIG. 1, the example wave guide assembly 74 includes the wave guide tube 76 that extends between end fittings 84. The end fittings 84 are coupled to a main transceiver 72 on one end and remote transceivers 75a and 75b on other ends. In this example, a first remote transceiver 75a is disposed and associated with the sensor assembly 78 and a second remote transceiver 75b is associated with a component 80. Each of the sensors 78 and the component 80 are in communication with the wave guide assembly 74 through a coupling 82. The coupling 82 provides for splitting a signal wave into different paths.

Referring to FIG. 3 with continued reference to FIG. 2, the example wave guide tube 76 is shown in cross-section and includes a wave propagation passage 88 that is disposed within an internal cavity 106. The example wave guide tube 76 is a hollow circular tube that includes the internal cavity 106 that in this example is of a circular cross-section 94. Within the internal cavity 106 is provided a wave guide housing 86. The wave guide housing 86 is a separate piece that defines the wave propagation passage 88. The wave guide propagation passage 88 includes a width 100 and a height 98. The width 100 and height 98 are provided with specific dimensions that correspond with the wave form that is transmitted there through. The wave propagation passage 88 may be filled with a dielectric material schematically shown at 85 that aids the transmission of a wave form. The dielectric material 85 may be of any know material and composition that aids in the transmission of the wave form.

In this example, the wave guide housing 86 is a separate piece from the outer housing 102. The wave guide housing 86 is inserted into the tubular housing 102 prior to the tube 76 being bent to a desired shape. Once the wave guide housing 86 is within the tubular housing 102, the specific desired shape of the wave guide tube 76 is formed. The wave guide housing 86 includes extensions 96 that contact interior surface of the internal cavity 106 to support the wave propagation passage 88 in a central location within the internal cavity 106. The extensions 96 may be welded or otherwise attached to the internal surface of the tube 76. Moreover, the extensions 96 define spaces 92a and 92b that are defined partially between the wave guide housing 86 and the internal surfaces of the tubular housing 102. The mentioned non-limiting example depicts one way to fabricate the waveguide system from multiple detail parts. Other fabrication techniques such as additive manufacturing techniques using DMLS (Direct Metal Laser Sintering) could also be used to fabricate a complete assembly. It should also be noted that more than one waveguide propagation passage 88 may be utilized within the waveguide tube for providing redundant channels.

On either side of the wave guide housing 86 are provided cavities 90a and 90b. These cavities are formed and defined between an outer surface of the wave guide housing 86 and the internal surfaces of the cavity 106. In this example, the cavities 90a and 90b are substantially half circles disposed on either side of the wave guide housing 86. The cavities 90a and 90b provide a space through which conductors or optic fibers 108 and 110 are routed. In this example, the conductors 108 and 110 provide electrical or optic power to a component sensor or other device that is coupled to the wave guide assembly. In this way, both electric, optic, power and control signals transmitted through the wave guide propagation passage 88 are disposed within a common conduit thereby eliminating the need for individual power wires to each component and sensor within the gas turbine engine.

Referring to FIGS. 4 and 5 with continued reference to FIG. 3, the example wave guide tube 76 is shown split in half to illustrate the wave guide housing 86 disposed within the internal cavity 106 of the tubular housing 102. The conductors or fibers 110a and 110b are routed within the passage or space that is defined between the wave guide housing 86 and internal surfaces of the tubular housing 102.

The conductors or fibers 110a and 110b are terminated at connectors 112 and 114 that are formed in end fitting 84 (FIG. 5). The end fitting 84 also includes a wave guide opening 120 that aligns with the wave guide propagation passage 88 to provide a continuous open passage for transmission of wave form signals.

Figure 6:
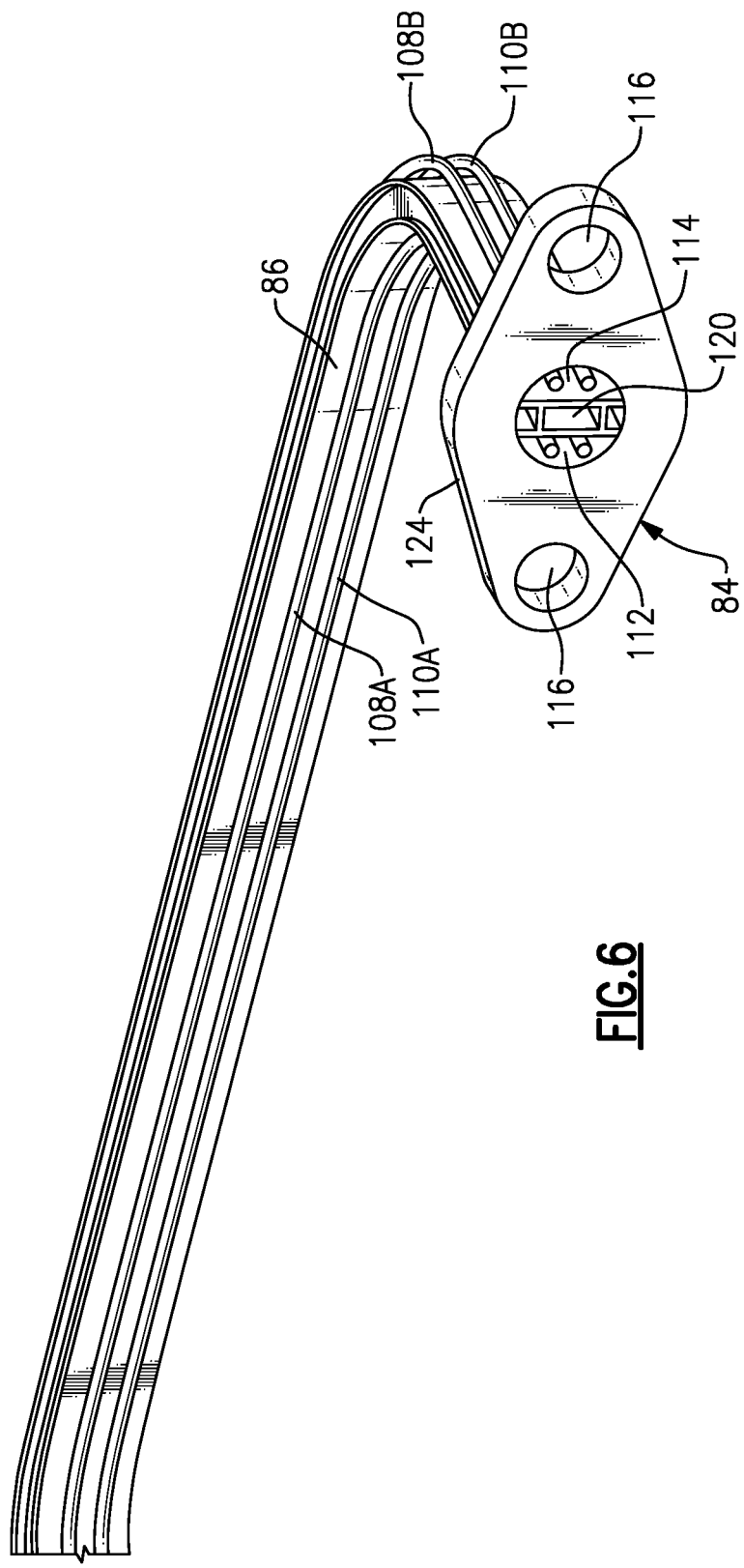
FIG. 6 is a sectional view of a wave guide tube and end fitting.

Referring to FIG. 6, another cutaway view illustrates the wave guide housing 86 along with the electrical or optic conductors without the tubular housing 102. In this view it can be seen that each side of the wave guide housing 86 defines a space through which electrical conductors or optic fibers 108a, 108b, 110a and 110b can be routed. Each of these power conductors are terminated at the end fitting 84 by connectors 112 and 114. The connectors 112, 114 correspond with the end fitting 84 to provide an interface that can be coupled to the transceivers, other wave guide tubes 76 or couplings 82 as required to split the wave guide into various sections to communicate with many components at the same time. Although the figures depict two pairs of conductors or optic fibers within cavities 90A and 90B, additional conductors or fibers could be implemented depending on the design needs.

Referring to FIGS. 7, 8, 9, and 10, the example end fitting 84 is shown and includes a tubular portion 126 that ends at a flange 124 including openings 116 utilized with threaded fasteners (not shown) to secure the various components of the tubular wave guide assembly 74 together. The flange 124 includes a face 118 that defines a mating surface for connection to other wave guide structures.

In this example, the end fitting 84 is of a female configuration and includes connectors 112 and 114 that provide female receptacles for termination of the electrical conduits or optic fibers. The wave guide opening 120 is provided at a central location that corresponds with the location of the wave guide propagation passage 88 through the wave guide tube 76. Above and below the wave guide in this embodiment are slots 122. The slots 122 receive tabs in another male configured end fitting to align the wave guide propagation passage 88 and opening 120.

Referring to FIGS. 11, 12, 13 and 14, a male configured end fitting 130 is shown that includes outwardly extending male pins 142 and tabs 144. The tabs 144 are disposed above and below a wave guide opening 138. Tabs 144 are received in slots 122 defined within the female end fitting 84 (FIG. 7) to align the end fittings 84, 130 and wave guide passages and openings.

The example end fitting 130 includes the face 136. From the face 136 extend the pins 142 along with the tabs 144. The end fitting 130 includes a tubular portion 134 that transitions into a flange 132. The flange 132 defines a face 136 coupled to another fitting, transceiver or coupling. The fitting 130 also includes openings 140 for fasteners. The tabs 144 are above and below the wave guide opening 138. The tabs 144 fit securely within the slots 122 to provide a precise alignment required to align the wave guide passages and openings. Moreover, the tabs 144 provide an alignment feature such that the connector pins 142 are aligned with corresponding openings in connectors 112 and 114 of the female end fitting 84.

Figure 8:
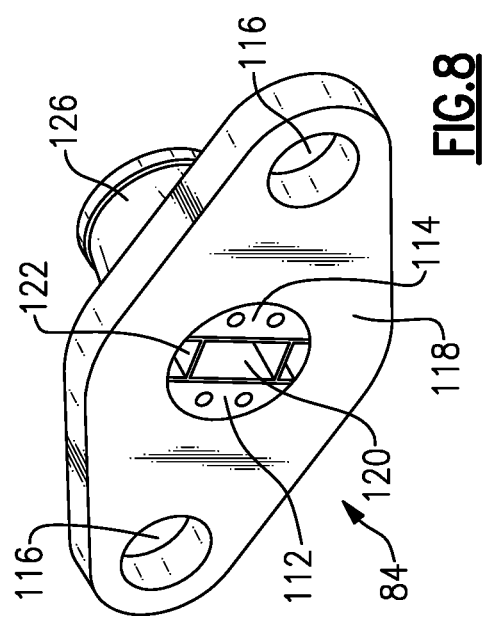
FIG. 8 is a front view of the example end fitting.
Figure 10:
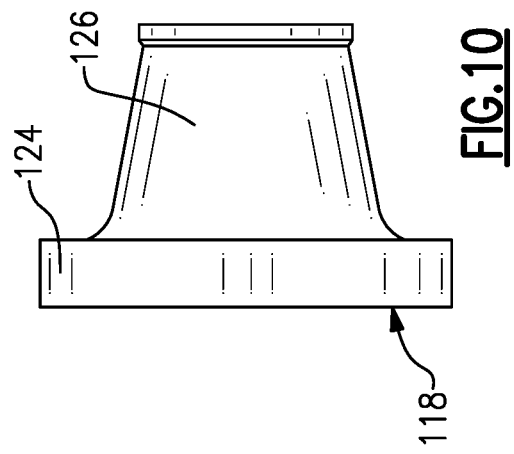
FIG. 10 is a top view of the example end fitting.
Figure 7:
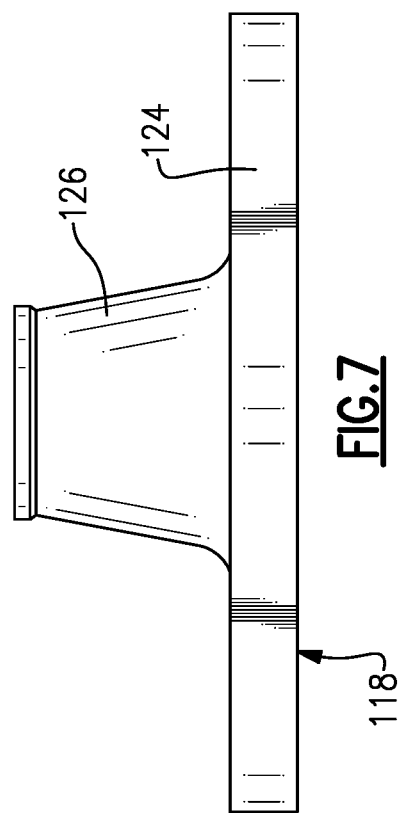
FIG. 7 is a perspective view of an end fitting.
Figure 9:
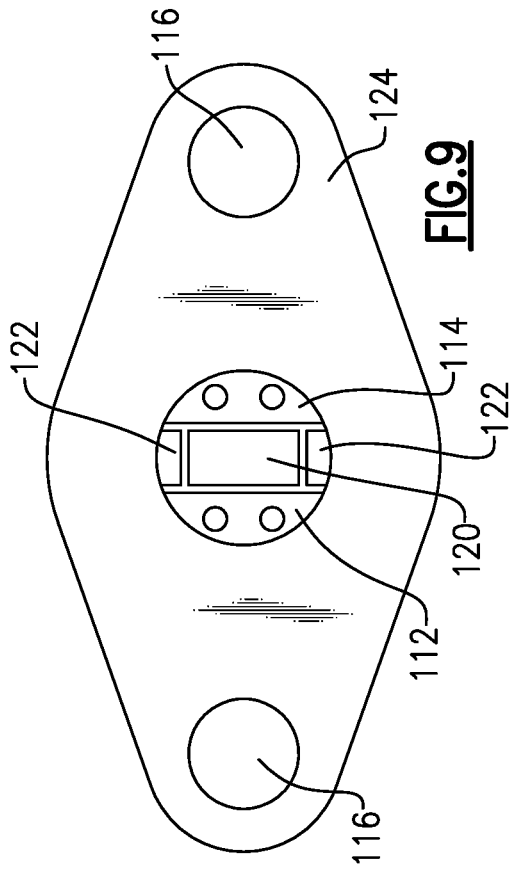
FIG. 9 is a side view of the example end fitting.
Figure 11:
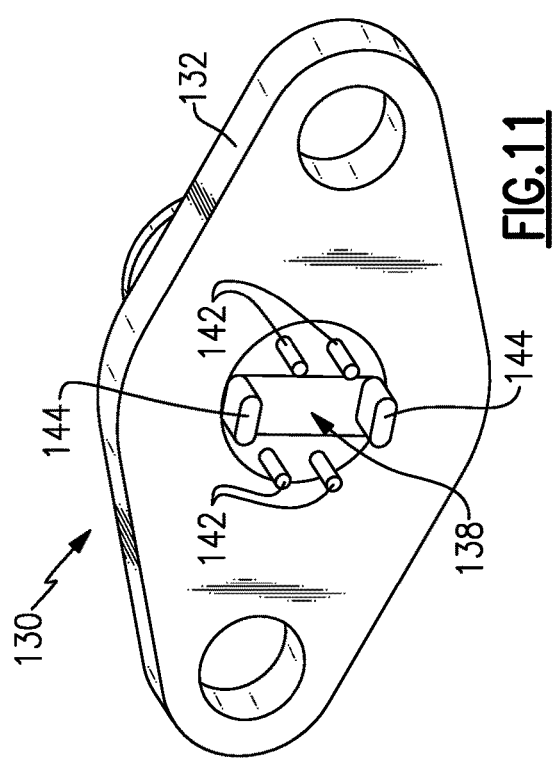
FIG. 11 is a perspective view of another example end fitting.
Figure 13:
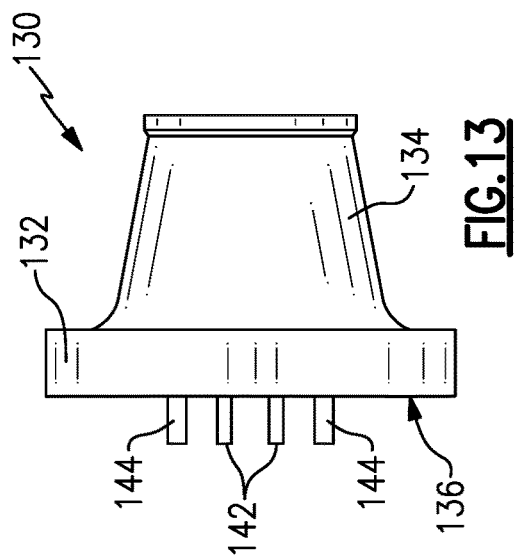
FIG. 13 is a side view of the example end fitting.
Figure 12:
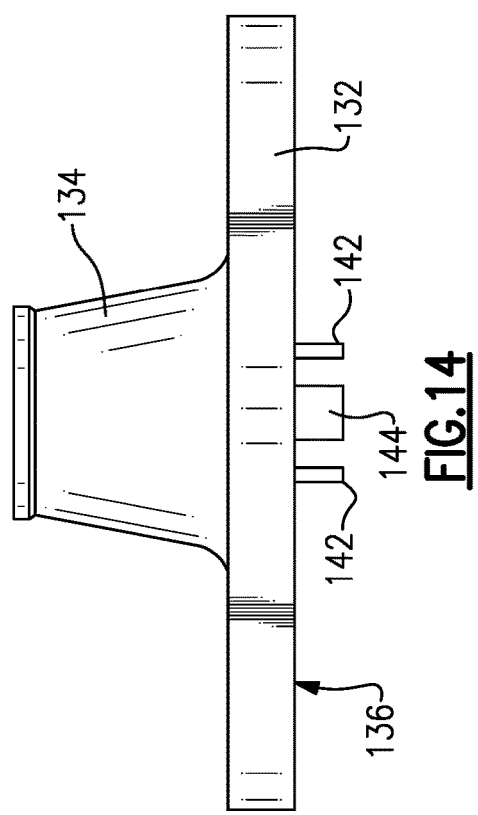
FIG. 12 is a front view of an example end fitting.
Figure 14:
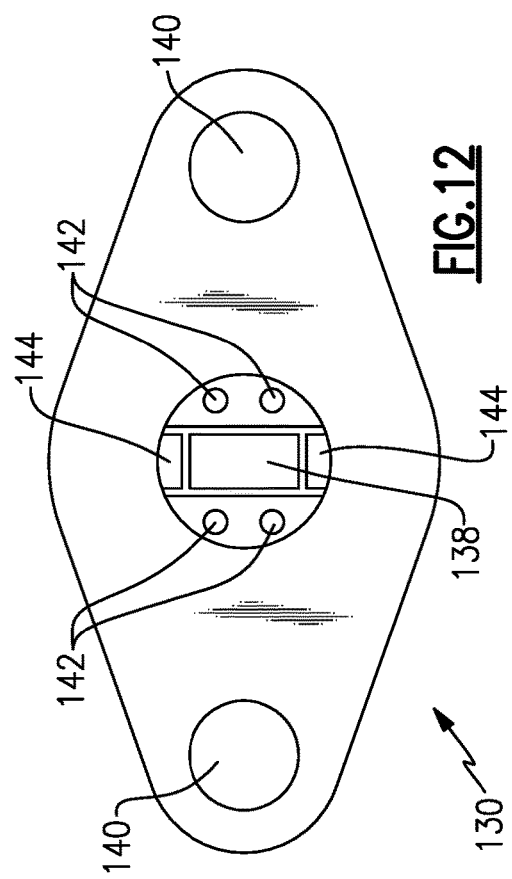
FIG. 14 is a top view of the example end fitting.
Figure 15:
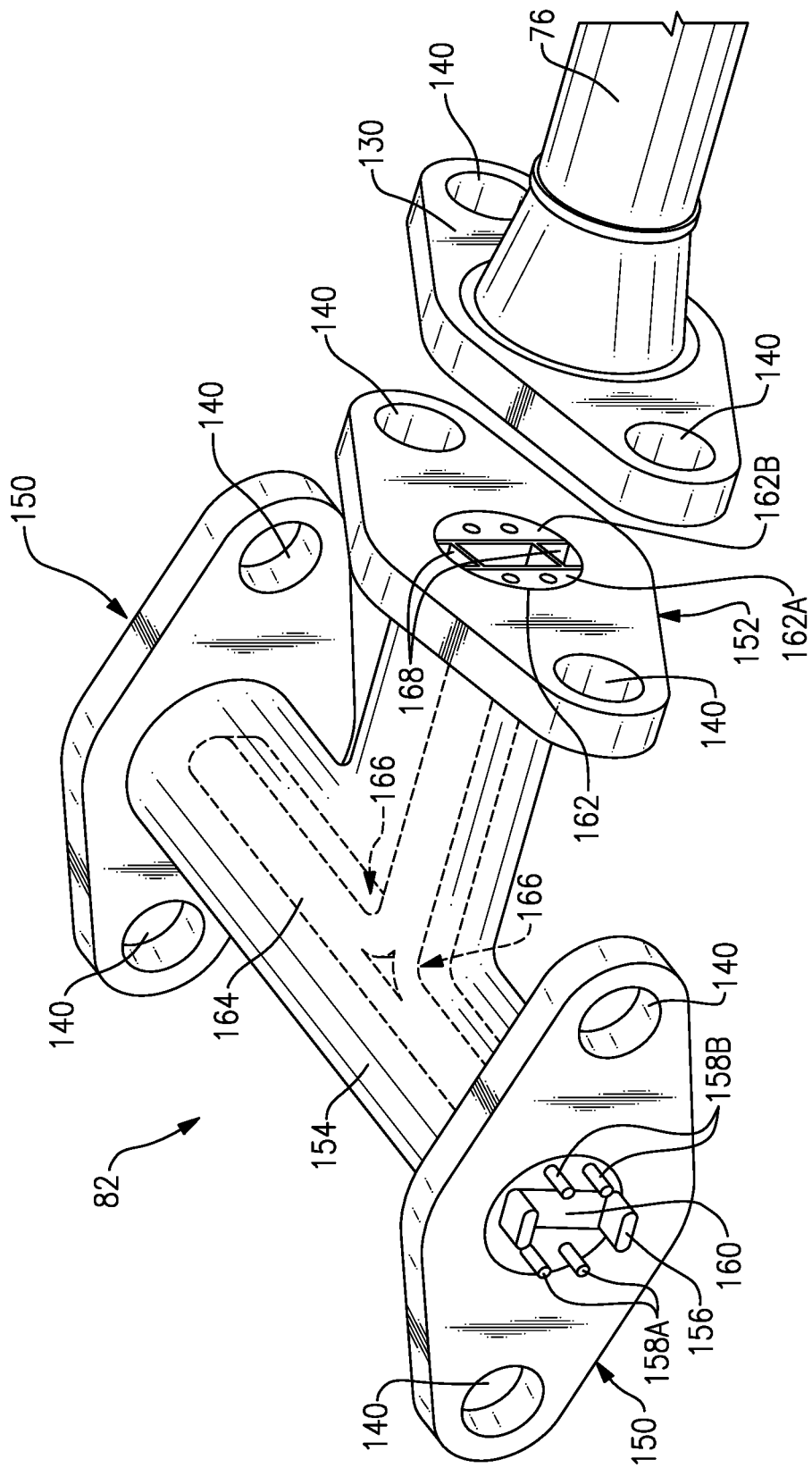
FIG. 15 is a perspective view of a coupling.
Figure 16:
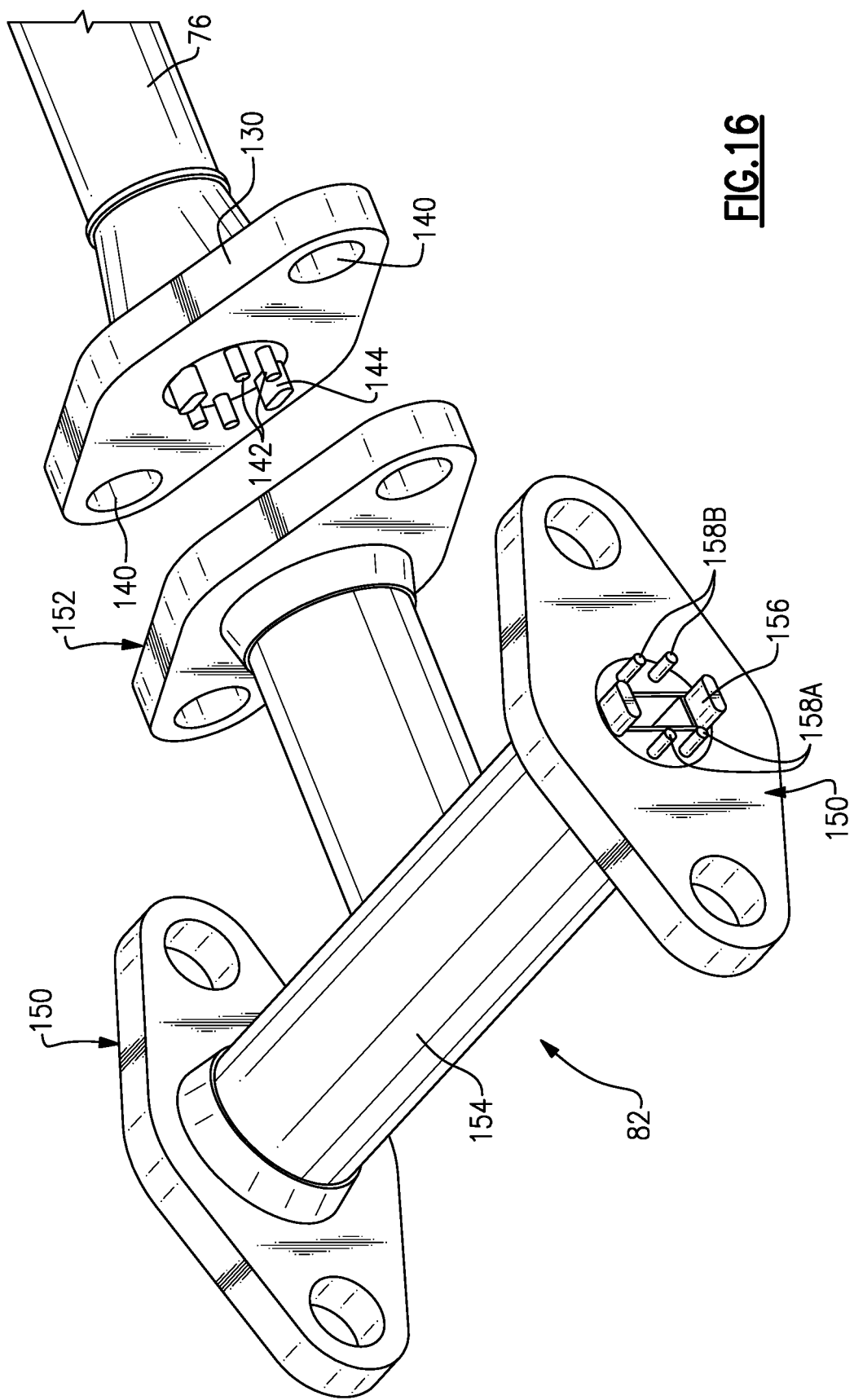
FIG. 16 is another perspective view of the example coupling.

Referring to FIGS. 15 and 16, the coupling 82 is illustrated and shown in association with the end fitting 130. In this example, the coupling 82 includes end faces 150 and 152. The end face 152 includes female connectors 162A and 162B that accept the outward extending pins 142 provided in the end fitting 130. In this example, the faces 150 disposed on either side of the coupling 154 include pins 158A, 158B and the tabs 156 that are receivable within a female end fitting 84 as illustrated in FIG. 8 The provided figures depict one non-limiting example of male/female combinations for interconnecting waveguide tubes. Design configurations for protecting power circuits during assemble may require many alternate configuration that would not be practical for illustration in a single document.

Figure 17:
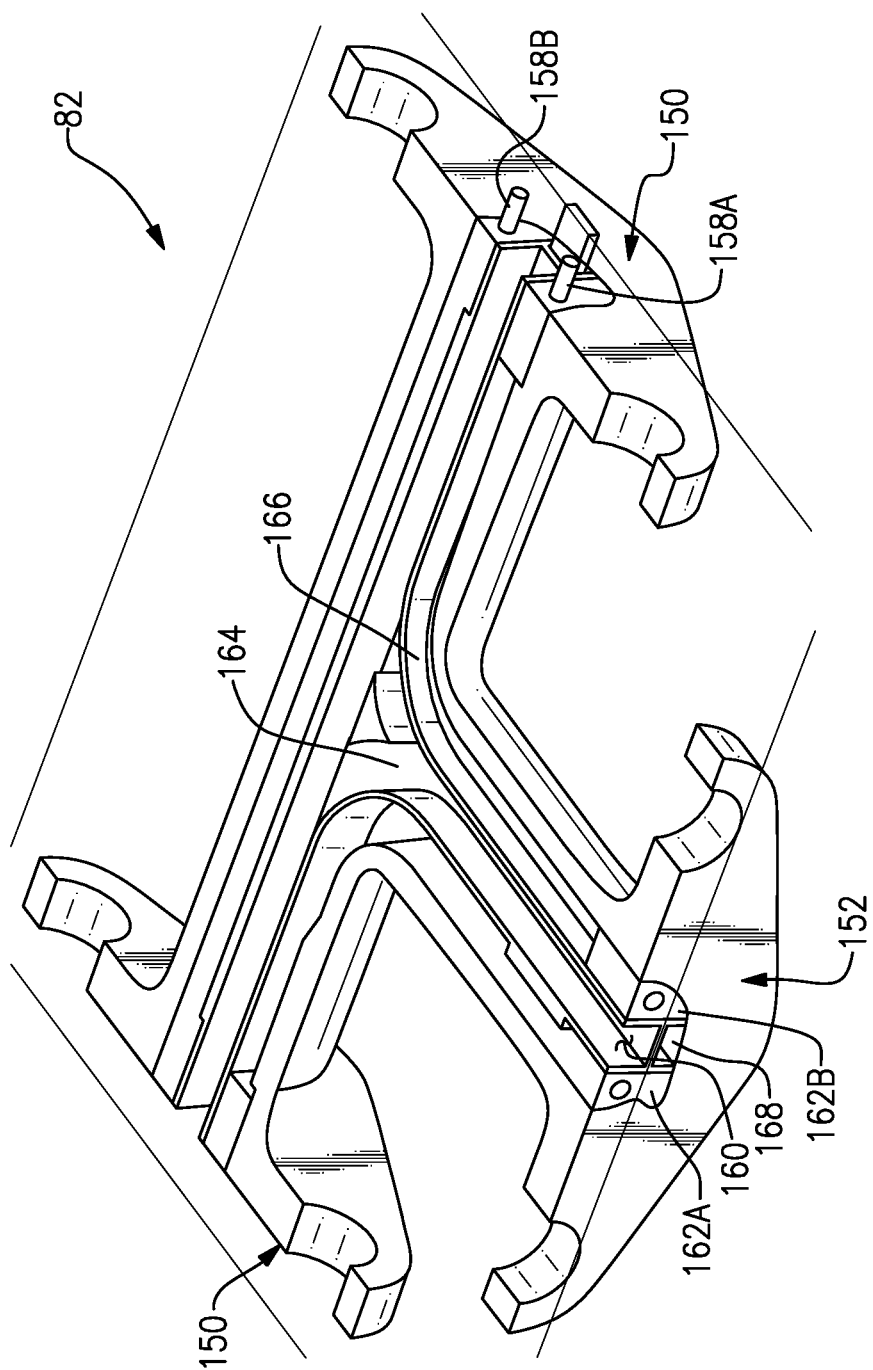
FIG. 17 is a partial cut-away of the example coupling.

Referring to FIG. 17 with continued reference to FIGS. 15 and 16, the coupling 82 includes wave propagation passage 164, that provides a smooth undisturbed passage for transmission of wave form signals between wave guide openings 160 at each end face 150, 152. The wave propagation passage 164 is configured to include the same cross-section as the wave guide housing 86. The wave propagation passage 164 within the coupling includes the additional curved structure 166 that provides the desired smooth transition between end faces 150.

The example coupling 82 provides for the splitting of the wave propagation passage 164 and also of the electrical or optic connections such that a common continuous wave propagation passage 164 extends between various components in the gas turbine engine enabling multiple frequencies to be transmitted to multiple components along a common protected transmission path defined by the wave guide assembly 74. As previously mentioned more than one channel of waveguide communication may be incorporated into the coupling 82.

Figure 18:
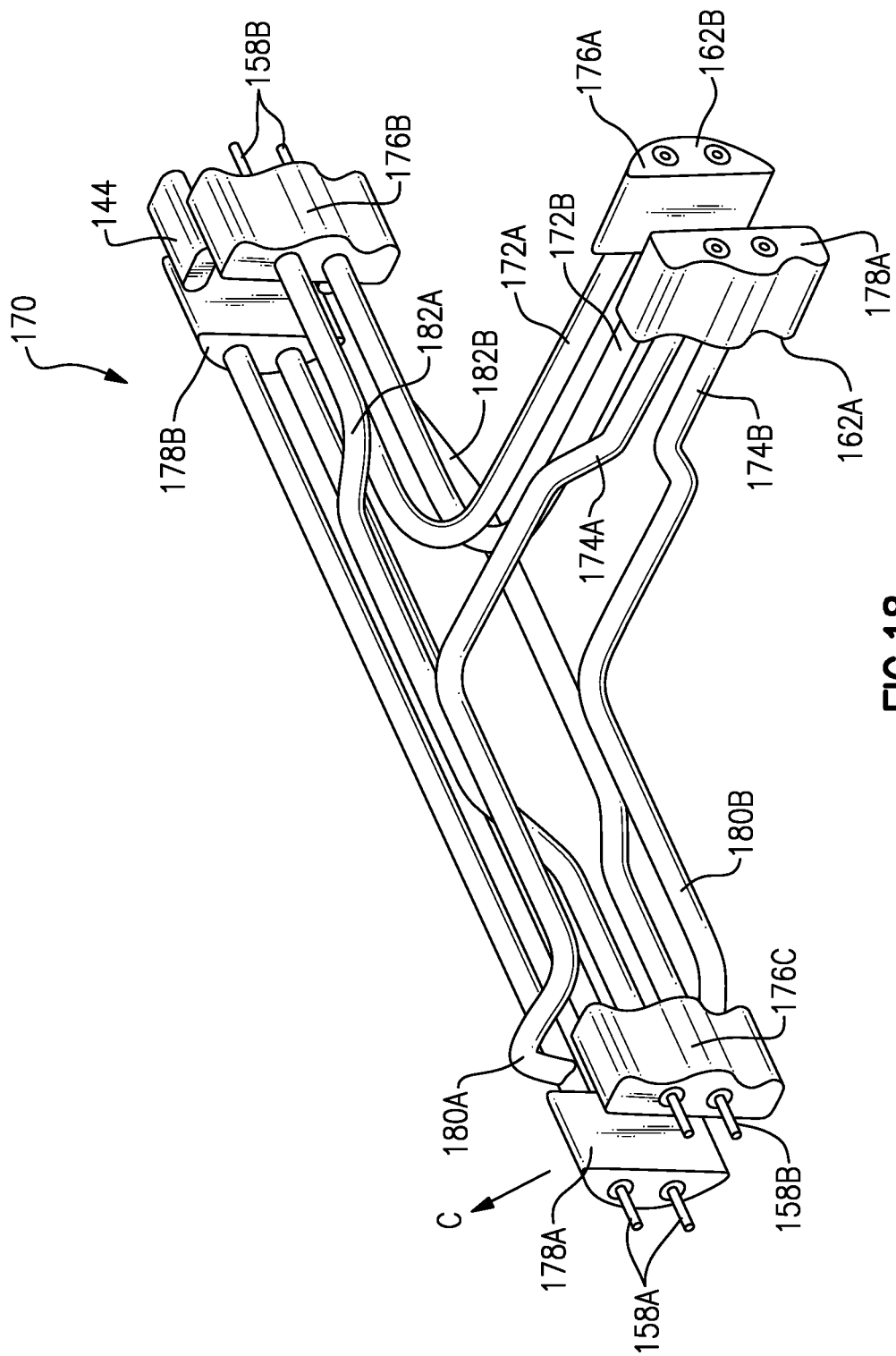
FIG. 18 is a perspective view of an example conductor assembly.

Referring to FIG. 18 with continued reference to FIGS. 15, 16 and 17, the coupling 82 includes a conductor assembly 170 that includes connectors 178A and 176A that correspond with the face 152. The connectors 178A and 176A in this embodiment include female pines 162A and 162B. The connector 178A is coupled to connectors 178B and 178C and corresponding end faces 150. The connectors 178A, 178B and 178C are connected by electrical conductors 174A and 174B. Crossover connections 180A and 180B provide the three-way connection between the connectors 178A, 178B and 178C. The connector 176A is similarly in electrical communication with connectors 176B and 176C at the end faces 150. Electrical conductors 172A and 172B extend between the three connectors 176A, 176B and 176C. Corresponding cross over connections 182A and 182B provide the three-way connection between the connectors 176A, 176B and 176C. It should be appreciated that although electrical conductors are discloses and described as an example embodiment other electrical communication structures such as optic fibers could also be utilized and are within the contemplation of this disclosure.

Accordingly, the example wave guide assembly provides a compact transmission path for communication of wave form signals and electric signals to multiple locations within a gas turbine engine that simplifies communication, reduces complexity and improves durability and performance of control functions of a gas turbine engine.

Although an example embodiment has been disclosed, a worker of ordinary skill in this art would recognize that certain modifications would come within the scope of this disclosure. For that reason, the following claims should be studied to determine the scope and content of this disclosure.

What is claimed is:

1. A wave guide assembly for a control and diagnostic system for a machine, the wave guide assembly comprising:
    a housing defining an exterior surface and an internal cavity extending between distal ends;
    at least one wave guide within the internal cavity defining a wave propagation passage for at least one wave form signal, wherein the wave propagation passage comprises a rectangular wave propagation passage in cross-section within the internal cavity; and
    at least one conductor within the internal cavity separate from the wave guide.

2. The wave guide assembly as recited in claim 1, including an end fitting attached to each end of the housing.

3. The wave guide assembly as recited in claim 2, including a coupling branching the wave propagation passage into two separate paths extending in different direction, the coupling including three ends with a wave propagation passage and one of an electrical power conductor and an optic fiber extending to each of the three ends.

4. The wave guide assembly as recited in claim 3, wherein each of the three ends of the coupling includes a face and each face includes a connector corresponding with the at least one conductor.

5. The wave guide assembly as recited in claim 1, wherein the wave propagation passage is a separate part inserted into the housing.

6. The wave guide assembly as recited in claim 1, including a dielectric within the wave propagation passage.

7. The wave guide assembly as recited in claim 1, wherein the wave propagation passage defines a size corresponding with a desired frequency range of the wave form signal.

8. The wave guide assembly as recited in claim 1, wherein the housing comprises a tube with a circular external cross-section and the wave propagation passage is contained within the cross-section.

9. The wave guide assembly as recited in claim 8, wherein outer walls of the wave propagation passage cooperate with interior walls of the internal cavity to define conductor passages for at least one of an electrical conductor and an optic fiber.

10. The wave guide assembly as recited in claim 9, where the conductor passages are defined on either side of the wave guide.

11. The wave guide assembly as recited in claim 9, wherein the conductor comprises one of an electrical conductor and an optic fiber disposed in each of the conductor passages.

12. The wave guide assembly as recited in claim 9, including support members supporting the wave propagation passage within the internal cavity, the support members defining cavities separated from the conductor passages.

13. A control and diagnostic system for a machine comprising:
    a main transceiver mounted proximate the machine, the transceiver generating and receiving radio frequency waves;
    a housing defining an exterior surface and an internal cavity extending between distal ends, a wave guide within the internal cavity defining a wave propagation passage for a wave form signal, and a conductor passage for at least one conductor extending within the internal cavity separate from the wave guide; and
    at least one remote transceiver attached to an end of the wave guide assembly and in communication with the main transceiver through a wave form signal communicated through the wave guide.

14. The control and diagnostic system as recited in claim 13, including an end fitting attached to each end of the housing for coupling the housing to the main transceiver at one end and to the at least one remote transceiver at another end and a coupling branching the wave propagation passage into two separate paths extending in different directions to a corresponding one of the at least one transceivers, the coupling including three ends.

15. The control and diagnostic system as recited in claim 13, wherein the wave guide comprise a rectangular wave propagation passage in cross-section within the internal cavity.

16. The control and diagnostic system as recited in claim 13, wherein the wave propagation passage comprises a circular wave propagation passage in a cross-section within the internal cavity.

17. The control and diagnostic system as recited in claim 13, wherein the wave propagation passage is a separate part inserted into the housing.

18. The control and diagnostic system as recited in claim 13, wherein the housing comprises a tube with a circular external cross-section and the wave propagation passage is contained within the cross-section.

* * * * *